United States Patent
Riesberg

(10) Patent No.: US 9,987,448 B1
(45) Date of Patent: Jun. 5, 2018

(54) TRACHEOSTOMY TUBE APPARATUS AND METHOD

(71) Applicant: Michael V. Riesberg, Pensacola, FL (US)

(72) Inventor: Michael V. Riesberg, Pensacola, FL (US)

( * ) Notice: Subject to any disclaimer, the term of this patent is extended or adjusted under 35 U.S.C. 154(b) by 661 days.

(21) Appl. No.: 13/962,013

(22) Filed: Sep. 19, 2013

Related U.S. Application Data

(63) Continuation of application No. 13/199,396, filed on Aug. 29, 2011.

(51) Int. Cl.
*A61M 16/00* (2006.01)
*A61M 16/04* (2006.01)

(52) U.S. Cl.
CPC ...... *A61M 16/044* (2013.01); *A61M 16/0051* (2013.01); *A61M 16/047* (2013.01); *A61M 16/0463* (2013.01); *A61M 16/0488* (2013.01)

(58) Field of Classification Search
CPC .. A61M 16/00; A61M 16/04; A61M 16/0402; A61M 16/0427; A61M 16/0434; A61M 16/044; A61M 16/0445; A61M 16/0456; A61M 16/0459; A61M 16/0465; A61M 16/0488; A61M 16/0497; A61M 16/06; A61M 16/0605; A61M 16/0627; A61M 16/0683–16/0694; A61M 25/10; A61M 25/1002–25/1018

See application file for complete search history.

(56) References Cited

U.S. PATENT DOCUMENTS

| | | | | |
|---|---|---|---|---|
| 4,498,473 A | * | 2/1985 | Gereg | A61M 16/04 128/207.14 |
| 4,762,130 A | * | 8/1988 | Fogarty | A61B 17/22032 604/103.07 |
| 5,642,730 A | * | 7/1997 | Baran | A61M 16/0463 128/200.23 |
| 2002/0014238 A1 | * | 2/2002 | Kotmel | A61M 16/04 128/204.18 |
| 2009/0260632 A1 | * | 10/2009 | Abnousi | A61M 16/04 128/207.15 |
| 2010/0288289 A1 | * | 11/2010 | Nasir | A61M 16/04 128/861 |

* cited by examiner

*Primary Examiner* — Jackie Tan-Uyen T Ho
*Assistant Examiner* — Ned T Heffner
(74) *Attorney, Agent, or Firm* — J. Nevin Shaffer, Jr.

(57) ABSTRACT

A tracheostomy tube apparatus and method includes an outer tube with a first end and a second end and an inside and an outside. Dual inflatable balloons are connected in spiral relation with the outside of the second end of the outer tube. An outer suction tube with more than one outer suction port is connected with the outer tube such that the more than one outer suction port captures secretions from the outside of the outer tube. An inner tube, conformed to fit within the outer tube, is provided. The inner tube has a first end and a second end and an inner suction tube with more than one inner suction port is connected with the inner tube such that the more than one inner suction port captures secretions from the inside of the inner tube.

13 Claims, 3 Drawing Sheets

TRACHEOSTOMY TUBE APPARATUS AND METHOD

CROSS REFERENCE TO RELATED APPLICATION

This application is a Continuation in Part of pending U.S. patent application Ser. No. 13/199,396 filed Aug. 29, 2011 entitled "Endotracheal Tube Apparatus and Method". The Applicant hereby claims the benefit of the non-provisional application under 35 U.S.C. § 120. The entire content of this non-provisional application is incorporated herein by this reference.

FIELD OF THE INVENTION

This invention relates to a tracheostomy tube apparatus consisting of an outer tube with a first end and a second end and an inside and an outside. Dual inflatable balloons are connected in spiral relation with the outside of the second end of the outer tube. An outer suction tube with more than one outer suction port is connected with the outer tube such that the more than one outer suction port captures secretions from the outside of the outer tube. An inner tube, conformed to fit within the outer tube, is provided. The inner tube has a first end and a second end and an inner suction tube with more than one inner suction port is connected with the inner tube such that the more than one inner suction port captures secretions from the inside of the inner tube.

BACKGROUND OF THE INVENTION

Tracheotomies are performed in hospital institutions on both adult and pediatric patients for airway obstruction, respiratory failure, trauma, failure to successfully wean from mechanical ventilation and neurologic impairment. Many patients in rehabilitation hospitals or tertiary care hospitals require tracheostomy for airway support. Although many tracheostomy patients are ambulatory and can function with an uncuffed tracheostomy tube, there are many hospitals or institutional based patients that require a tracheostomy tube that has a balloon cuff. This is true for both pediatric and adult patients. Most prior art "cuffed" tracheostomy tubes utilize a high volume/low pressure cuff in order to reduce oral secretions from aspirating into the lungs as well as to provide positive pressure ventilation.

A tracheostomy is inserted by open surgical procedure directly into the trachea below the level of the vocal cords. Once the tracheostomy tube is inserted into the trachea, the balloon cuff (near the distal end opening of the tube) is inflated with air.

Although risks versus benefits of tracheostomy are weighted far to the benefits side, Applicant has, among others, identified many problems with prior art tracheostomy design in pediatric and adult settings such as:

1. Aspiration of bacteria-laden oral secretions or food particles through the vocal cords and into the trachea. Although a balloon cuff on the prior art tracheostomy tube can reduce aspiration, it does not always prevent it. Furthermore, a patient can be prone to "silent" aspiration whereby these secretions track into the lungs and cannot be coughed clear. Many of these secretions can accumulate between the outer wall of the tube and the lining of the trachea, an area where conventional oral suctioning or intra-luminal suctioning cannot access.

2. Injury to the trachea mucosa with current art subglottic suction tubes. Prior art open suction ports can grab delicate trachea mucosa and create trauma and edema of the trachea mucosa from the exposed suction ports found in prior art tubes.

3. Trauma and granulation tissue formation at the surgical opening or trachea, results in tracheostome narrowing or subglottic stenosis. Firm plastic prior art tubes create friction and trauma on contact points with the tracheostome. Once tracheostome stenosis, subglotic stenosis, or granulation tissue occurs, the corrective surgery that is called for is often mired with complications.

4. Circumferential pressure and ischemia against the wall of the trachea. Interruption of blood flow to the trachea coupled with impaired lymphatic flow will result in a bacteria-laden biofilm developing between the balloon cuff and the trachea mucosa. If the cuff is not regularly deflated, the biofilm triggers an inflammatory reaction that can trigger granulation tissue formation and eventual scar tissue formation (subglottic stenosis). A tracheoesophageal fistula can also form between the esophagus and the trachea at the balloon cuff segment. These complications are very expensive to remedy and carry a high mortality rate.

5. Circumferential cuff pressure against ciliated columnar epithelium of the trachea produces a tourniquet effect that compromises viability of mucociliary clearance (cleaning) of the trachea and lungs; a leading cause of ventilator acquired pneumonia.

6. Constant balloon cuff pressure in a single/isolated region of the trachea. Constant balloon cuff pressure is often required by prior art devices for mechanical ventilation in ICU and surgical settings. The problem that often results from the use of prior art tubes with single inflatable balloon cuffs is a "flail segment" or a weakened cartilage wall of the trachea in the area of the inflated balloon. One prior art remedy to this serious problem is to simply move the balloon to a site below the flail segment. However, this practice often simply expands the area of injury to the trachea. Furthermore, the prior art tracheostomy tubes are often limited to the amount of additional length you have with the tube and the balloon cuff.

7. Accumulation of secretions below the balloon cuff. The human mucociliary belt of the lining of the trachea tends to drive lung secretions in an upward direction toward the larynx and the mouth. Prior art tracheostomy tubes which have a single balloon cuff stop the upward clearance of mucous secretions at the balloon level. Although separate time consuming intra-luminal suctioning can recover some of these secretions, the constant pressure of the single balloon of the prior art can weaken or paralyze mucociliary in a circumferential segment coincident with the area of balloon contact. Such compromise can increase the risk of aspiration and/or pneumonia.

8. Accumulation of secretions within the inner cannula (internal tube) of the tracheostomy. Currently, periodic suctioning by nursing staff or the patient is the state of the art for cleaning the inner tube. Nonetheless, these efforts are not fully satisfactory and mucous drainage can still occlude the inner tracheostomy tube and increase the risk of aspiration pneumonia.

It, therefore, is an object of the invention to provide an improved tracheostomy tube that addresses each of the above listed problems associated with prior art tracheostomy tubes and that is practical and not excessively complicated.

SUMMARY OF THE INVENTION

Accordingly, the tracheostomy tube apparatus of the present invention, according to one embodiment, includes an outer tube with a first end and a second end and an inside and an outside. Dual inflatable balloons are connected in spiral relation with the outside of the second end of the outer tube. An outer suction tube with more than one outer suction port is connected with the outer tube such that the more than one outer suction port captures secretions from the outside of the outer tube. An inner tube, conformed to fit within the outer tube, is provided. The inner tube has a first end and a second end and an inner suction tube with more than one inner suction port is connected with the inner tube such that the more than one inner suction port captures secretions from the inside of the inner tube.

It should be understood that terms used herein are given their common meaning as known in the art. Thus, "tube" is known to mean a form that has an inside and an outside with an interior space created by the sides of the tube. Typically, the tube is cylindrical in shape but it may be any shape desired or found effectual for the circumstance. "Inflatable balloon" identifies a device that expands under pressure and that resumes its original size and form upon deflation, as does a regular balloon.

According to another aspect of the invention, the dual inflatable balloons include a first inflatable balloon and a second inflatable balloon connected in spiral relation with the second end of the outer tube where the first inflatable balloon is connected with the second end above the second inflatable balloon. "Spiral relation", as used herein, refers to a form created by an elongated wrapping of one item around another item. The stripes on a barber pole form a spiral in relation to the pole, for example only and not by way of limitation.

In one aspect, the first inflatable balloon is separately inflatable apart from the second inflatable balloon. In a further aspect, the outer suction tube includes at least two outer suction ports at the second end of the outer tube with at least one outer suction port at the first inflatable balloon and at least one outer suction port at the second inflatable balloon.

In another aspect, the at least one outer suction port is recessed below the outside of the outer tube and in another aspect, the at least one outer suction port is recessed below the outside of the outer tube within the spiral of the first inflatable balloon and the second inflatable balloon.

In one aspect, the outer suction tube and the inner suction tube are conformed to connect to form a single first end suction port. In another aspect, the invention further includes a gel collar surrounding at least a segment of said outside of said outer tube. As used herein the term "gel" is used to identify a material that is not rigid but soft and yielding. A medical quality silicone is suitable such as that offered under the brand names Silflex and Mepifel, for example only and not by limitation. It is noted that in plastic surgery, surface application of such soft gels to a wound promotes healing and reduces scar tissue formation. Preferably, the gel collar of the present invention is applied to the length of the tube that would most likely be in surface contact with the vocal cord mucosa.

In another aspect, the dual inflatable balloons are connected with an inflation tube such that the dual inflatable balloons are controllable to alternately inflate and deflate such that as one balloon is inflated the other balloon is deflated.

According to another embodiment, a tracheostomy tube apparatus consists of an outer tube with a first end and a second end and an inside and an outside. A first inflatable balloon is connected in spiral relation with the outside of the second end of the outer tube. A second inflatable balloon is connected in spiral relation with the outside of the second end of the outer tube. A first outer suction tube with a first outer suction port is connected at the second end of the outer tube in relation with the first inflatable balloon where the first outer suction port captures secretions from the outside of the outer tube. A second outer suction tube with a second outer suction port is connected at the second end of the outer tube in relation with the second inflatable balloon where the second outer suction port captures secretions from the outside of the outer tube. A first inflation tube is connected with the first inflatable balloon such that the first inflatable balloon is controllable to alternately inflate and deflate. A second inflation tube is connected with the second inflatable balloon such that the second inflatable balloon is controllable to alternately inflate and deflate. An inner tube, conformed to fit within the outer tube, is provided, the inner tube with a first end and a second end and an inner suction tube with more than one inner suction port is connected with the inner tube such that the more than one inner suction port captures secretions from the inside of the inner tube.

In another aspect of this embodiment, the first inflatable balloon is connected with the second end of the outer tube above the second inflatable balloon. In one aspect, the invention further includes a gel collar connected with the outside of said tube.

As used herein, the term connected "in relation with" describes a connection in which one element is connected next to or in close proximity with another element. That is, there are no specific locations that are absolutely required for the required suction ports, for example, only that they be located in proximity to or relation with the listed elements.

In one aspect of this invention, the first inflatable balloon is connected with the second end above the second inflatable balloon. Again, as shown in the figures, here the two balloons are sequentially located along the tube one after the other. Obviously, it may be that other configurations are desired and useful too such as overlapping or entwined relationships.

In one aspect, the first outer suction port and the second outer suction port are recessed below the outside of the outer tube within the spiral of the first inflatable balloon and the second inflatable balloon. In another aspect, the first outer suction tube, the second outer suction tube and the inner suction tube are conformed to connect to form a single first end suction port.

In a further aspect, a monitor device is provided. A pump device and a suction device are provided and both are connected with the monitor device. The pump device is connected with the first inflatable balloon and the second inflatable balloon for inflating and deflating the balloons and the suction device is connected with the first outer suction tube, the second outer suction tube and the inner suction tube for applying suction to the tubes.

In another aspect the invention includes a monitor device and a pump device and a suction device both connected with the monitor device. The pump device is connected with the first inflatable balloon and the second inflatable balloon and the suction device is connected with the first outer suction tube, the second outer suction tube and the inner suction tube at the single first end suction port.

According to another embodiment, a method for using a tracheostomy tube consists of:

a. providing an outer tube with a first end and a second end and an inside and an outside; dual inflatable balloons connected in spiral relation with the outside of the second end of the outer tube; an outer suction tube with more than one outer suction port connected with the outer tube such that the more than one outer suction port captures secretions from the outside of the outer tube; an inner tube, conformed to fit within the outer tube, the inner tube with a first end and a second end; and an inner suction tube with more than one inner suction port connected with the inner tube such that the more than one inner suction port captures secretions from the inside of the inner tube; and b. connecting a pump device and a suction device with the outer tube and the inner tube where the pump device is connected with the dual inflatable balloons and where the suction device is connected with the outer suction tube and the inner suction tube.

In one aspect, the invention further includes the step of connecting the pump device and the suction device to a monitor device. As used herein the term "monitor device" is used to describe a device conformed to monitor and control the operation of the apparatus of the invention and control the timing and operation of the pump and suction devices as will be more fully described hereafter with regard to the figures. Suffice to say, any electro-mechanical devices now known or hereafter developed for monitoring, pumping and suctioning are included within the scope of the present invention. Such monitors, pumps and suction devices are well within the ability of those of ordinary skill in the art.

In one aspect, the outer suction tube and the inner suction tube are conformed to connect to form a single first end suction port and the suction device is connected with the single first end suction port. In another aspect, the dual inflatable balloons are connected with an inflation tube such that the dual inflatable balloons are controllable to alternately inflate and deflate such that as one balloon is inflated the other balloon is deflated.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
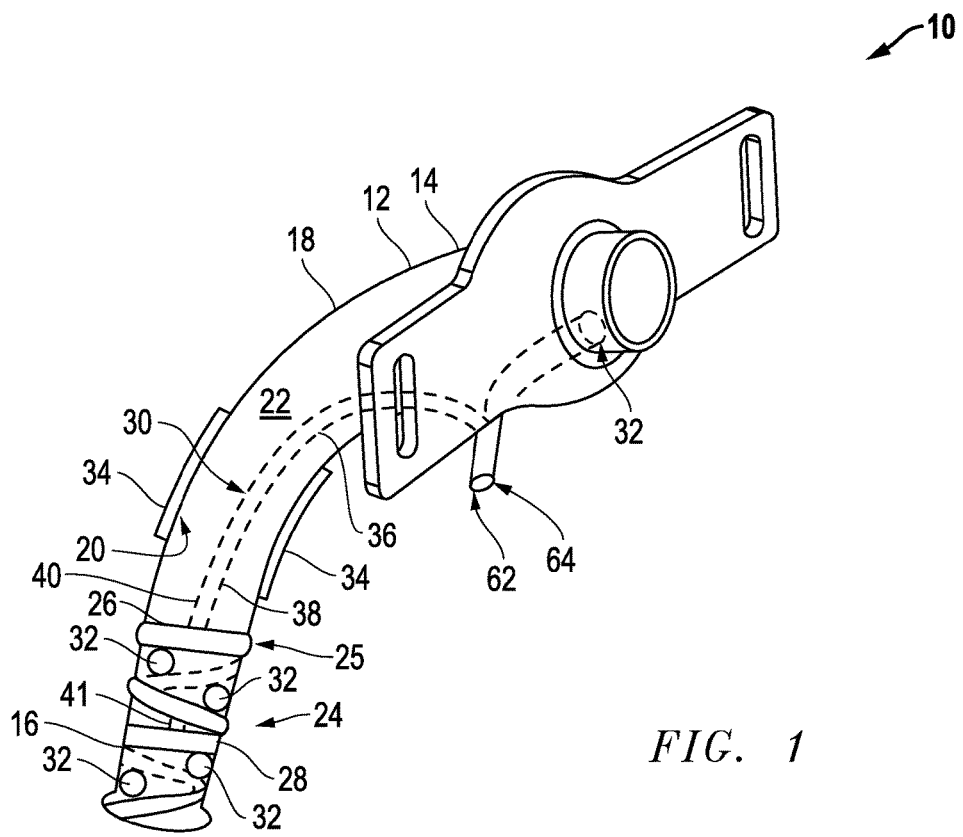
FIG. 1 perspective, partial section view of the outer tube of the tracheostomy tube of the present invention.

The preferred embodiment of the present invention is illustrated by way of example in FIGS. 1-4. With specific reference to FIG. 1, tracheostomy tube apparatus 10 includes an outer tube 12. Outer tube 12 includes a first end 14 and a second end 16 and is formed of a pliable material such as plastic, for example only and not by way of limitation. The outer tube 12 has an exterior surface 18 and an interior surface 20. The outer tube 12 includes an empty interior space 22 created by those surfaces. Outer tube 12 may be cylindrically shaped as illustrated or any other useful form.

Preferably, the tracheostomy tube apparatus 10 includes dual inflatable balloons 24 in the form of a first inflatable balloon 26 and a second inflatable balloon 28. As used herein, again, the term "inflatable" describes an object that is capable of holding a gas, such as air as with a hot air balloon, for example only and not by way of limitation. The term "balloon" is used to describe an object that is expandable but does not rupture upon ordinary use as with a common plastic or rubber balloon. Upon the release or relaxation of the incoming air, the balloon deflates to its resting size and upon the introduction of air it re-inflates. Thus, dual inflatable balloons 24 of the present invention may be inflated and deflated over and over again without failure. They may be constructed from any pliable and expandable material that returns to its original uninflated form upon the release of air such as a flexible, elastic plastic and rubber for example only.

Importantly, dual inflatable balloons 24 are connected in spiral relation with the exterior surface 18 of outer tube 12 and around outer tube 12 at the second end 16 of outer tube 12 as illustrated. In one embodiment, the first inflatable balloon 26 is connected to outer tube 12 above second inflatable balloon 28 as illustrated.

Figure 3:
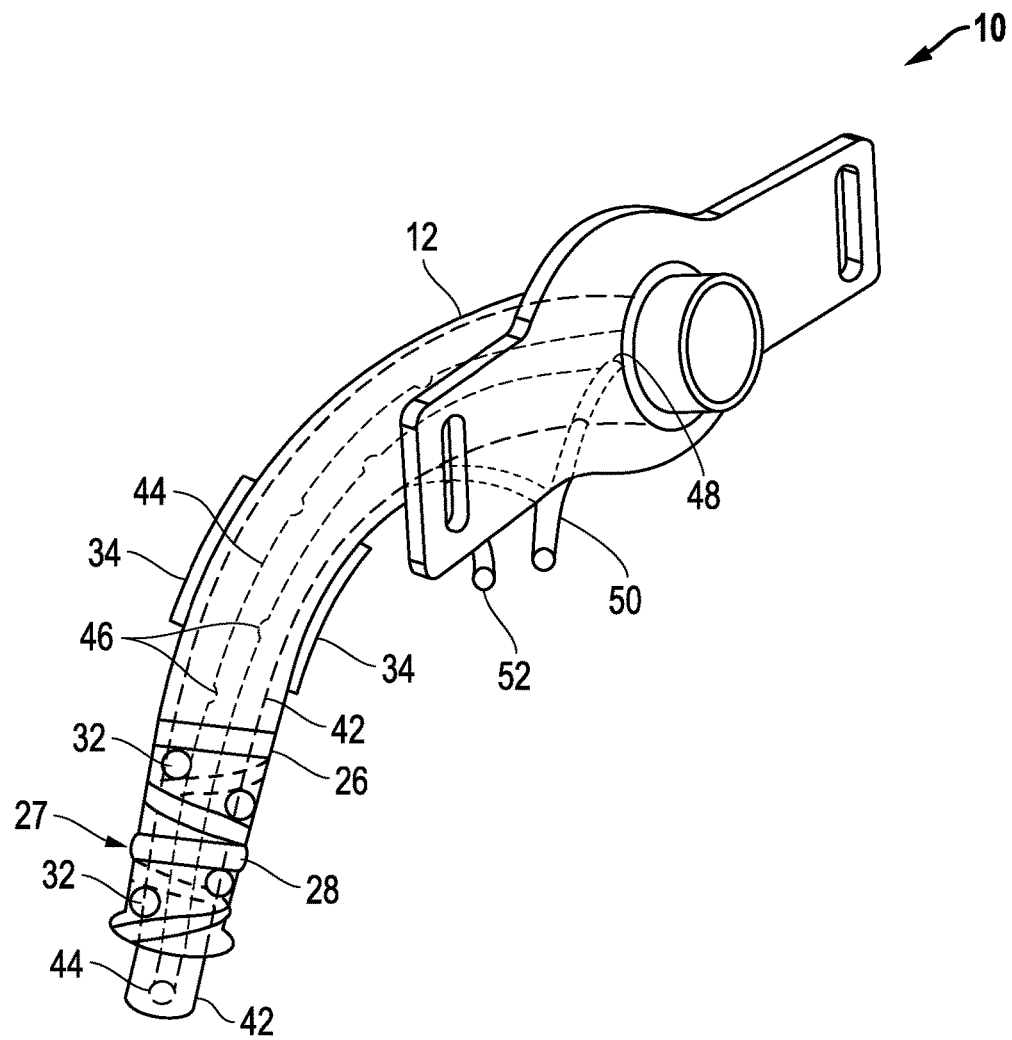
FIG. 3 is a side view of the inner tube connected inside the outer tube of the invention of FIG. 1.

FIG. 1 illustrates this configuration and also shows the embodiment in which dual inflatable balloons 24 are separately and independently inflatable. FIG. 1 shows first inflatable balloon 26 inflated and extended away from the exterior surface 18 of outer tube 12 forming a thin cuff 25 and second inflatable balloon 28 deflated. FIG. 3 shows first inflatable balloon 26 deflated and second inflatable balloon 26 inflated and extended away from the exterior surface 18 of outer tube 12 and forming a thin cuff 27. In this case, when the outer tube 12 is in place in a patient, the expanded cuffs 25 and 27 of inflatable balloons 24 and 26 alternately and minimally contact the patient and seal outer tube 12 against air leaks. Preferably in time with respiration of the patient, second inflatable balloon 28 inflates and then first inflatable balloon 26 deflates as illustrated in FIG. 3. As a result, an ever changing contact is maintained with the patient without applying constant pressure at a single location and causing damage as described above.

Still referring to FIG. 1, tracheostomy tube apparatus 10 also includes, according to a preferred embodiment, an outer suction tube 30 with more than one outer suction port 32. The outer suction tube 30 is connected with outer tube 12 in any convenient manner. As shown in the figures, outer suction tube 30 starts on the outside of outer tube 12 and passes through the exterior surface 18 and into the interior space 22 of outer tube 12. The length of outer suction tube 30 then extends down the interior 22 of outer tube 12 and ends at outer suction ports 32. That is, there is preferably more than one outer suction port 32 and, preferably, outer suction ports 32 capture secretions from the outside of outer tube 12. In one embodiment, outer suction tube 30 includes at least one outer suction port 32 at the first inflatable balloon 26 and at least one outer suction port 32 at the second inflatable balloon 28. Certainly there can be more outer suction ports 32 as desired. Importantly, outer suction ports 32 are recessed below the outside of outer tube 12. Preferably this "recess" is created by locating the outer suction ports 32 within the spiral form of the dual inflatable balloons 24. This recess ensures that the sensitive throat lining is not directly contacted at the time suction is applied to the outer suction ports 32. The recess is emphasized or exaggerated, of course, when the dual inflatable balloons 24 are inflated but exists even when they are deflated.

Applicant has determined that there is a very advantageous effect that results from the spiral attachment of the inflatable balloons. An unexpected vortex or swirling of fluids is channeled into the space created by the pulsating inflatable balloons. This helps ensure that fluids are driven to the outer suction ports 32 and increases the effectiveness of the suctioning. That is the geometry of the spiral shape of the balloons spins the airflow between the outer tube 12 and the trachea and, applicant has found, separates solid mucous very effectively so as to be easily captured at the outer suction ports 32. Additionally and importantly, the spiral shape of the dual balloons 24 minimizes balloon contact area with the mucosa of the trachea.

FIG. 1 (and FIG. 3 as will be discussed more fully hereafter) also illustrates a gel collar 34. Gel collar 34 surrounds at least a segment or part of the exterior surface 18 of outer tube 12. As illustrated, gel collar 34 is shown connected with outer tube 12 below the first end 14 and above the dual inflatable balloons 24 at the second end 16 of outer tube 12. Applicant has found that the gel collar 34 may be applied to approximately five centimeters of the outer tube 12 that are most likely to be in surface contact with sensitive areas of the throat. Certainly, more or less of outer tube 12 may be covered with gel collar 34 as desired.

Gel collar 34 is required to be softer than outer tube 12. That is outer tube 12 may be pliable but must be rigid enough to enable insertion and withdrawal of the outer tube 12 in use. As discussed above, prior art tubes even though pliable still can cause considerable harm. Thus, the function of gel collar 34 is to provide a more pliable softer contact surface. Gel collar 34 may be made of any soft, pliable, yet sturdy, material such as medical quality silicone or any other such material now known or hereafter developed as detailed above.

Preferably, tracheostomy tube apparatus 10 also includes an inflation tube 38 such that the dual inflatable balloons 24 are controllable to alternately inflate and deflate such that as one balloon is inflated the other balloon is deflated as discussed above. Thus, preferably, there is a first inflation tube 40 and a second inflation tube 41. The first inflation tube 40 is connected with the first inflatable balloon 26 and the second inflation tube 42 is connected with the second inflatable balloon 28.

Figure 2:
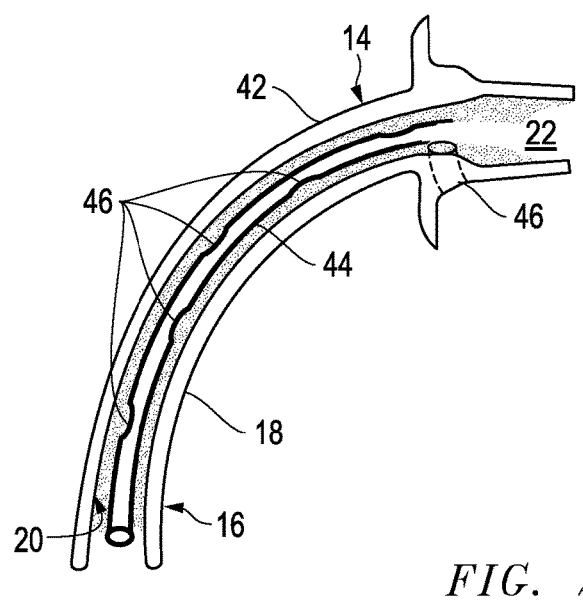
FIG. 2 is a side section view of the inner tube of the invention of FIG. 1.

Referring now to FIG. 2, inner tube 42 includes a first end 14, a second end 16, and exterior surface 18, interior surface 20 and interior space 22 as does outer tube 12. Inner suction tube 44 with more than one inner suction port 46 is connected with inner tube 42 in the interior space 22 of inner tube 42 such that the more than one inner suction port 46 captures secretions from the inside of inner tube 42.

In one important aspect of the invention, the outer suction tube(s) 30 and the inner suction tube 44 are conformed to connect to form a single first end suction port 48 at the first ends 14 of outer tube 12 and inner tube 42 when the inner tube 42 is connected inside outer tube 12 as shown more clearly in FIG. 3. As a result, as single suction tube 50 when connected at single first end suction port 48 applies suction to all the outer suction ports 32 and the inner suction ports 46 through single suction tube 50.

Still referring, to FIG. 3, a similar single first end inflation hub 52 may be provided for connection with inflation tubes 38 either one or both. Where a first inflation tube 40 and a second inflation tube 41 are provided, the inflation hub 52 collects the two tubes but the proper operation of the invention requires that the tubes be separately inflatable. Thus, the two inflation tubes may be gathered within a single covering tube but, again, kept separate.

Figure 4:
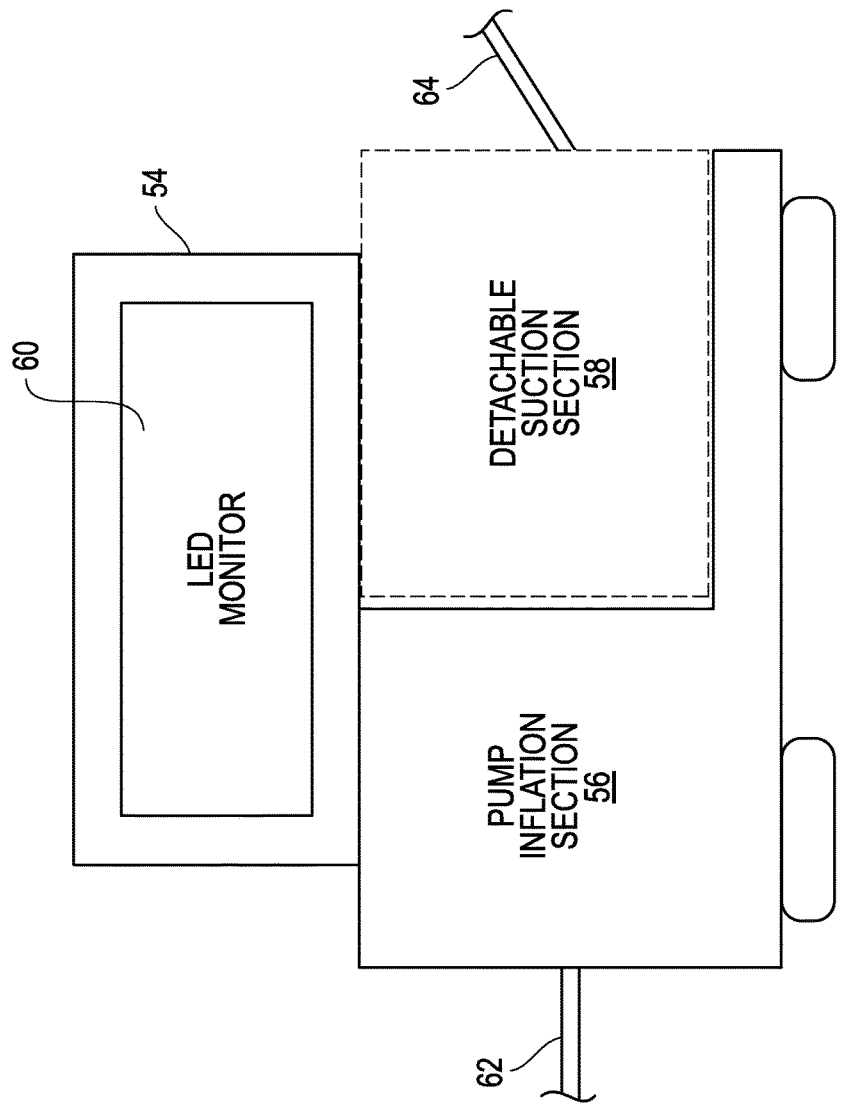
FIG. 4 is a schematic diagram of a monitor, a pump and a suction device according to one embodiment of the invention of FIG. 1.

Referring now to FIG. 4, other features of the invention are discussed. In a preferred embodiment, a monitor device 54 is provided and a pump device 56 and a suction device 58 are both connected with the monitor device 54. Pump device 56 is connected with the dual inflatable balloons 24, first inflatable balloon 26 and second inflatable balloon 28, and suction device 58 is connected with outer suction tube 30 as a first suction tube connection and with inner suction tube 44 as a second suction tube connection preferably at single first end suction port 48.

Pump device 56 pumps air, for example only, when activated to inflate the inflatable balloons 24. When not pumping air, air is free to escape from pump device 56. It may also be that pump device 56 may be reversed to actively evacuate or suck air from a particular balloon to assist with deflation.

Suction device 58 applies a suction to draw fluids into the suction tubes and provides a container for collection of extracted fluids. Suction device 58 may be detachable from the assembly shown in FIG. 4 to allow easy disposal of fluids and cleaning.

Monitor device 54 is an electronic monitor as is known in the art, such as a computer. As such monitor device 54 is connected with and controls the operation of pump device 56 and suction device 58 while at the same time monitoring pressures and providing visual feedback to the operator as to pressures, timing or inflation and deflation cycles, and the like. An LED screen 60 in monitor device 54 is provided for observing the function and status of the devices as desired.

By way of continued explanation, Applicant's tracheostomy tube apparatus 10 addresses all of the problems set forth herein with regard to prior art adult, adolescent, and pediatric balloon cuffed tracheostomy tubes. The Applicant's design is an efficient and is not overly complex in refinements and improvements on prior art design.

With prior art tubes, pressure and friction against the skin and mucosal surfaces of the tracheostome has resulted in granulation tissue and scar tissue formation. This dreaded complication, known as tracheostome stenosis or subglottic tracheal stenosis, is a costly complication to remedy and is at risk for morbidity and mortality. Soft material such as medical quality silicone provides a cushioning effect against pressure and a lubricating, effect against friction. The gel collar 34 of the present tracheostomy device also promotes wound healing as it has been shown in plastic surgery that the application of silicone sheeting to healing wounds reduces scar tissue formation. Gel collar 34, again, may be made of soft, slippery, lubricating material and/or include a layer of lubricating material that is bacteriostatic such as medical grade silicone impregnated with an antibiotic.

Circumferential pressure against the wall of the trachea is an inescapable fact of prior art adult, adolescent, or pediatric cuffed tracheostomy tubes. The result, again, is ischemia to a long and circumferential segment of trachea mucosa. To overcome this problem, Applicant's device includes dual inflatable balloons 24, preferably in spiral configuration, with thin, small seal cuffs 25 and 27. The unique spiral design prevents circumferential ischemia from interrupting mucociliary clearance of the trachea. The spiral design with the thin seal cuffs 25 and 27 further reduces circumferential pressure that can result in granulation tissue formation, circumferential subglottic stenosis, and circumferential tracheosmalacia (flail segment).

The pressure within the spiral inflatable balloons 26 and 28 is accurately and constantly determined by monitor device 54 so that the seal is maintained for positive pressure ventilation but over inflation of over pressure of the balloons 24 and seal cuffs 25 and 27 is prevented. Applicant has determined that accurate monitoring of cuff pressure with prior art high volume-low pressure balloon cuffs is a heretofore daunting and time consuming task.

Still further, the spiral design of the present invention creates a vortex channel for a surprisingly effective suction of secretions that accumulate between the outer tube 12 and the trachea. Applicant has also noted that prior art tubes that incorporate a means of subglottic suctioning are prone to obstruction due to the exposed suction port adhering to the mucosa of the trachea. Furthermore, suction applied directly to the trachea mucosa can result in trauma and edema to the trachea. Thus, the structure of Applicant's invention in which the outer suction ports 32 are recessed within the channels of the spirals of the balloons 26 and 28 prevent them from directly contacting the mucosa of the trachea.

Additionally, by sequential inflation and deflation of the dual inflatable balloons 24, cuff pressure is alternated and intermittent pressure relief is provided. As a result, ischemia of the trachea mucosa is minimized or eliminated altogether. Nonetheless, by alternating inflation and deflation between the two balloons 26 and 28 (or more as desired) by means of monitor device 54 and pump device 56, a cuff seal is maintained at all times for positive pressure ventilation. As proper pressure is important, it is understood that monitor device 54 is connected with or provided with pressure sensors as are known and not disclosed further herein. Pressures may be quantitatively displayed on LED screen 60 or on a module of an ICU vital signs monitor device as is known or in any other useful manner. The timing of the inflation cycles may be set, for example only, on the monitor device 54 with a "mode" button to display "set balloon inflation timing", "set balloon inflation pressure", "set suction pressure", "purge suction tubing" and the like. Buttons may be used to set seconds/minutes on inflation timing, pressure in cm H2O and the like as well. Further, suction may be operated from a standard hospital wall suction system or or and independent, portable suction unit of any known or hereafter developed design.

Moreover, the accumulation of secretions and biofilm between the outer tube 12 and the wall of the trachea is prevented by means of vortex suction at the location of the dual inflatable balloons 24. When each spiral balloon inflates, it helps drive the secretions within the channels formed by the balloon. The shape of the suction channel is a cyclone or vortex. In a conventional prior art balloon endotracheal or tracheostomy cuff, the mucociliary belt that clears tracheal mucous in an uphill direction is stopped at the level of the balloon cuff. After the prior art balloon cuff has been inflated for a prolonged period of time, the mucociliary belt becomes weakened or even paralyzed even after cuff deflation. Impairment of mucociliary clearance increases the risk of aspiration pneumonia associated with prolonged use of cuffed tracheostomy tubes. As described herein, Applicant's device captures the secretions from the prior art dead space above their single balloon and between the wall of the outer tube 12 and the wall of the trachea.

Another important element of the present invention is the common inflation connecting tubing 62 that incorporates the inflation tubes 36, first inflation tube 38 and second inflation tube 40 after the inflation tubes exit the outer tube 12 on their way to pump device 56. Likewise common suction connection tubing 64 incorporates outer suction tubes 30 and inner suction tube 44. Preferably common suction connection tubing 54 connects with single first end inflation hub 52 such that only a single tube, common suction connection tubing 64, is required to be connected with suction device 58.

In a preferred embodiment then, there are two separate inflation tubes, first inflation tube 40 and second inflation tube 41, for connection with and operation of first inflatable balloon 26 and second inflatable balloon 28. Further, there are, preferably, two outer suction tubes 30 connected with outer suction ports 32, one outer suction tube 30 for each inflatable balloon 24. These outer suction tubes 30 are combined into one tube preferably before single first end suction port 48 Also, there is one inner suction tube 44. Thus, there are at least four separate tubes coming out of outer tube 12. To overcome the cumbersome nature of the four separate tubings, Applicant prefers that the four separate tubing section converge at some point into a single "cable". Thus, even the common inflation connection tubing 62 and common suction connection tubing are preferably enclosed in a single "cable shortly after leaving tracheostomy tube apparatus 10 outer tube 12 until divided again at the point of connection with pump device 56 and suction device 58. Various connection means are known to ensure that suction tubing is connected to suction tubing and inflation/deflation tubing is connected to inflation/deflation tubing and erroneous cross connections can not occur. Tubing and connections are to be made, as should be easily understood, to connect with tubing present in each and every medical venue, ICU, ambulances, personal CPAP devices and the like, and Applicant's invention easily accommodates freestanding and portable iterations.

Applicant has noted a significant problem with current art cuffed tracheostomy tubes: maintaining a constant, accurate balloon cuff pressure. Intra-balloon electrical pneumatic pressure sensors 66, for example only, are connected with pump device 56 and monitor device 54 to monitor continually and accurately balloon cuff pressure. The pump device 56 can be set to deliver predetermined balloon cuff pressures while timing and controlling inflation and deflation of the dual inflatable balloons 24. The balloon cuff pressure may be monitored by monitor device 54 or any other device deemed useful such as hand held devices, CPAP devices or hospital monitors so long as the device is conformed to receive and display the data.

Other aspects of the invention include use of disposable elements that come in contact with patient excretions, such as tubes and tubing. Other elements, the monitor, pump and suction devices are designed to be portable and reusable.

Monitor device 54 uses any programmable device such as a computer microchip, for example only, to control the operation of the pump device 56 and suction device 58. The LED screen 60 displays appropriate messages and alerts, balloon cuff inflation pressures, timing of inflation and deflation of the dual inflatable balloons 24, suction pressures and the like. Setting the pressures and sensing them and adjusting them is accomplished by and is a proper function of monitor device 54. Sensors 66 in the dual inflatable balloons 24 enable the monitor device 54 to adjust inflation pressures to the selected setting. Furthermore, sensors in the suction section as for example at the suction device 58 enable the monitor device 54 to monitor and adjust those pressures as well.

Monitor device 54 may display alerts to include, for example only and not by way of limitation, "first balloon malfunction", "second balloon malfunction", "power failure", "outer tube suction malfunction", "inner tube suction malfunction", "battery low", and "high pressure resistance".

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:
1. A tracheostomy tube apparatus comprising:
   a. an outer tube, wherein said outer tube is a continuous cylindrical tube with a length, with a first end and a second end, wherein said first end and said second end are spaced apart by said length of said outer tube, and an inside surface and an outside surface, wherein the outside surface forms the outermost continuous surface of a tracheostomy tube;
   b. dual inflatable balloons connected one after the other without overlapping connection with each other in spiral relation on the outside surface of said second end of said outer tube such that each of the dual inflatable balloons wraps around said tube in at least one complete spiral with each inflatable balloon forming a suction channel on the outside surface of said outer tube and such that said dual inflatable balloons form intermittent contacting surfaces on the outside surface of said outer tube along a portion of the length of said outer tube at said second end;
   c. an outer suction tube with more than one outer suction port transfixing said outer tube such that said more than one outer suction port captures secretions from the outside surface of said outer tube;
   d. an inner tube, conformed to fit within said outer tube, said inner tube with a first end and a second end and an inside surface and an outside surface; and
   e. an inner suction tube with more than one inner suction port located within said inner tube such that said more than one inner suction port captures secretions from the inside surface of said inner tube.

2. The apparatus of claim 1 wherein said more than one outer suction port is recessed below the outside surface of said outer tube.

3. The apparatus of claim 1 wherein said outer suction tube and said inner suction tube are conformed to connect to form a single first end suction port.

4. The apparatus of claim 1 further including a gel collar surrounding at least a segment of said outside surface of said outer tube.

5. The apparatus of claim 1 wherein said dual inflatable balloons are connected with an inflation tube such that said dual inflatable balloons are controllable to alternately inflate and deflate such that as one balloon is inflated the other balloon is deflated.

6. The apparatus of claim 1 wherein the dual inflatable balloons include a first inflatable balloon and a second inflatable balloon connected in spiral relation one after the other with said second end of said outer tube wherein said first inflatable balloon is connected with said outside surface of said outer tube at said second end and said second inflatable balloon is connected with said outside surface of said outer tube along a separate length of said outer tube at said second end.

7. The apparatus of claim 6 wherein said first inflatable balloon is separately inflatable apart from said second inflatable balloon.

8. The apparatus of claim 6 wherein said outer suction tube includes at least two outer suction ports at said second end of said outer tube with at least one outer suction port in said suction channel at said first inflatable balloon and at least one outer suction port in said suction channel at said second inflatable balloon.

9. The apparatus of claim 6 wherein said more than one outer suction port is recessed below the outside surface of said outer tube within said suction channels of the first inflatable balloon and the second inflatable balloon.

10. A method for using a tracheostomy tube comprising:
    a. providing an outer tube, wherein said outer tube is a continuous cylindrical tube with a length, with a first end and a second end, wherein said first end and said second end are spaced apart by said length of said outer tube, and an inside surface and an outside surface, wherein the outside surface forms the outermost continuous surface of a tracheostomy tube; dual inflatable balloons connected one after the other without overlapping connection with each other in spiral relation on the outside surface of said second end of said outer tube such that each of the dual inflatable balloons wraps around said tube in at least one complete spiral with each inflatable balloon forming a suction channel on the outside surface of said outer tube and such that said dual inflatable balloons form intermittent contacting surfaces on the outside surface of said outer tube along a portion of the length of said outer tube at said second end; an outer suction tube with more than one outer suction port transfixing said outer tube such that said more than one outer suction port captures secretions from the outside surface of said outer tube; an inner tube, conformed to fit within said outer tube, said inner tube with a first end and a second end and an inside surface and an outside surface; and an inner suction tube with more than one inner suction port connected with said inner tube such that said more than one inner suction port captures secretions from the inside surface of said inner tube; and
    b. connecting a pump device and a suction device with said outer tube and said inner tube wherein said pump device is connected with said dual inflatable balloons and wherein said suction device is connected with said outer suction tube and said inner suction tube.

11. The method of claim 10 wherein said dual inflatable balloons are connected with an inflation tube such that said dual inflatable balloons are controllable to alternately inflate and deflate such that as one balloon is inflated the other balloon is deflated.

12. The method of claim 10 further including connecting said pump device and said suction device to a monitor device.

13. The method of claim 12 wherein said outer suction tube and said inner suction tube are conformed to connect to form a single first end suction port and said suction device is connected with said single first end suction port.

* * * * *